United States Patent
Repka

(10) Patent No.: US 9,907,998 B2
(45) Date of Patent: Mar. 6, 2018

(54) WRIST DEVICE HAVING HEART ACTIVITY CIRCUITRY

(71) Applicant: Polar Electro Oy, Kempele (FI)

(72) Inventor: Mikko Repka, Oulu (FI)

(73) Assignee: POLAR ELECTRO OY, Kempele (FI)

( * ) Notice: Subject to any disclaimer, the term of this patent is extended or adjusted under 35 U.S.C. 154(b) by 0 days.

(21) Appl. No.: 14/713,480

(22) Filed: May 15, 2015

(65) Prior Publication Data
US 2016/0332025 A1   Nov. 17, 2016

(51) Int. Cl.

| G08B 21/00 | (2006.01) |
|---|---|
| A63B 24/00 | (2006.01) |
| G08B 7/06 | (2006.01) |
| G06K 9/00 | (2006.01) |
| A61B 5/024 | (2006.01) |
| G06F 1/32 | (2006.01) |
| G06F 3/01 | (2006.01) |
| G06F 3/03 | (2006.01) |
| G06F 21/32 | (2013.01) |
| G06F 3/0346 | (2013.01) |
| G06F 21/35 | (2013.01) |
| H04M 1/725 | (2006.01) |
| A61B 5/11 | (2006.01) |

(Continued)

(52) U.S. Cl.
CPC ...... *A63B 24/0062* (2013.01); *A61B 5/02416* (2013.01); *A61B 5/02438* (2013.01); *A61B 5/1112* (2013.01); *A61B 5/1118* (2013.01); *A61B 5/681* (2013.01); *G06F 1/3287* (2013.01); *G06F 3/014* (2013.01); *G06F 3/017* (2013.01); *G06F 3/0304* (2013.01); *G06F 3/0346* (2013.01); *G06F 21/32* (2013.01); *G06F 21/35* (2013.01); *G06K 9/00228* (2013.01); *G06K 9/00355* (2013.01); *G08B 7/06* (2013.01); *H04M 1/7253* (2013.01); *A61B 5/6817* (2013.01); *A63B 2024/0071* (2013.01); *H04L 63/0861* (2013.01); *H04W 12/06* (2013.01)

(58) Field of Classification Search
CPC .................................................. A63B 24/0062
USPC ............. 340/407.1, 691.1, 691.8; 455/575.6, 455/556.1
See application file for complete search history.

(56) References Cited

U.S. PATENT DOCUMENTS

| 6,535,605 B1 * | 3/2003 | Ghassabian ............ H04B 1/385 379/433.07 |
|---|---|---|
| 2012/0194976 A1 | 8/2012 | Golko et al. |

(Continued)

FOREIGN PATENT DOCUMENTS

| CN | 103179265 A | 6/2013 |
|---|---|---|
| CN | 103558749 A | 2/2014 |
| EP | 2779605 A1 | 9/2014 |

OTHER PUBLICATIONS

ZenWatch Manager—Cover to Mute, https://www.asus.com/support/FAQ/1009166, pp. 1-4.

*Primary Examiner* — Jeffery Hofsass
(74) *Attorney, Agent, or Firm* — Hoffmann & Baron, LLP

(57) ABSTRACT

A method includes: receiving, by a wrist device, a notification of an event, wherein the notification is indicated to a user of the wrist device; in response to receiving the notification, initiating at least one measurement; determining, based on the at least one measurement, that a predetermined condition is met; and in response to the determining that the predetermined condition is met, performing an action having an effect on the indication of the notification.

25 Claims, 7 Drawing Sheets

(51) Int. Cl.
*A61B 5/00* (2006.01)
*H04L 29/06* (2006.01)
*H04W 12/06* (2009.01)

(56) References Cited

U.S. PATENT DOCUMENTS

2014/0120983 A1    5/2014   Lam
2014/0171156 A1    6/2014   Pattikonda et al.

* cited by examiner

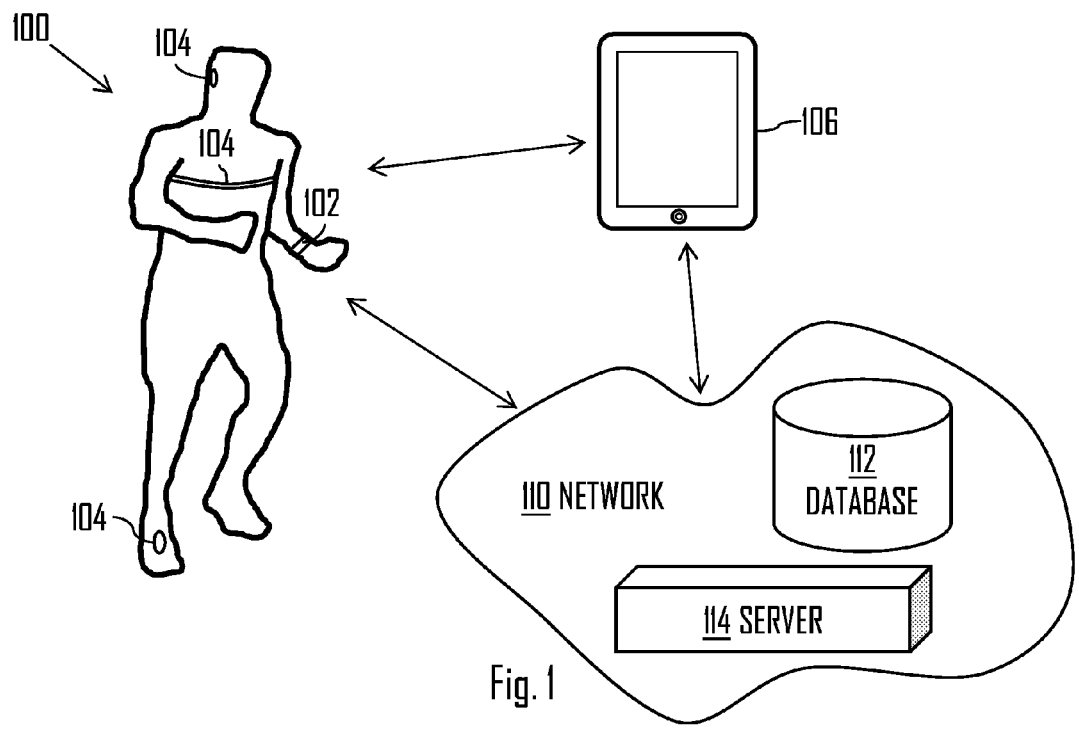

WRIST DEVICE HAVING HEART ACTIVITY CIRCUITRY

BACKGROUND

Field

This invention relates to wrist devices. More particularly, the invention relates to wrist device notifications.

Description of the Related Art

Wrist devices are becoming more popular among users for different purposes. Wrist devices may be used to illustrate notifications to their user. As the amount of different notifications increases, it may be beneficial to enhance the way the wrist devices handle notifications.

SUMMARY

According to an aspect, there is provided a wrist device comprising: at least one processor and at least one memory including a computer program code, wherein the at least one memory and the computer program code are configured, with the at least one processor, to cause the wrist device to perform operations comprising: receiving a notification of an event, wherein the notification is indicated to a user of the wrist device; in response to receiving the notification, initiating at least one measurement; determining, based on the at least one measurement, that a predetermined condition is met; and in response to the determining that the predetermined condition is met, performing an action having an effect on the indication of the notification.

According to an aspect, there is provided a method comprising: receiving, by a wrist device, a notification of an event, wherein the notification is indicated to a user of the wrist device; in response to receiving the notification, initiating at least one measurement; determining, based on the at least one measurement, that a predetermined condition is met; and in response to the determining that the predetermined condition is met, performing an action having an effect on the indication of the notification.

Some embodiments are defined in the dependent claims.

One or more examples of implementations are set forth in more detail in the accompanying drawings and the description below. Other features will be apparent from the description and drawings, and from the claims.

BRIEF DESCRIPTION OF DRAWINGS

In the following embodiments will be described in greater detail with reference to the attached drawings, in which FIG. 1 illustrates a physical activity measurement scenario to which embodiments of the invention may be applied;

FIG. 2 illustrates a block diagram according to an embodiment of the invention;

DETAILED DESCRIPTION

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

FIG. 1 illustrates a heart activity measurement system to which embodiments of the invention may be applied. Referring to FIG. 1, a user 100 may wear a wearable device 102, such as a wrist device 102. The wrist device 102 may be, for example, a smart watch, a smart device, and/or activity tracker apparatus.

In an embodiment, the wrist device 102 is an activity tracker apparatus that is not necessarily used in a wrist of the user 100.

The wrist device 102 may be used to monitor physical activity of the user 100 by using information from external sensor device(s) 104 and/or from internal sensor(s) comprised in the wrist device 102. It may be possible to receive physical activity-related information from a network 110, as the network may comprise, for example, physical activity-related information of the user 100 and/or some other user(s). Thus, the wrist device 102 may be used to monitor physical activity-related information of the user 100 and/or the other user(s). Naturally, one or more of the external sensor device(s) 104 may be worn by the other user(s), and thus information received from said one or more sensor device(s) 104 may be monitored from the wrist device 102 by the user 100.

Figure 3:
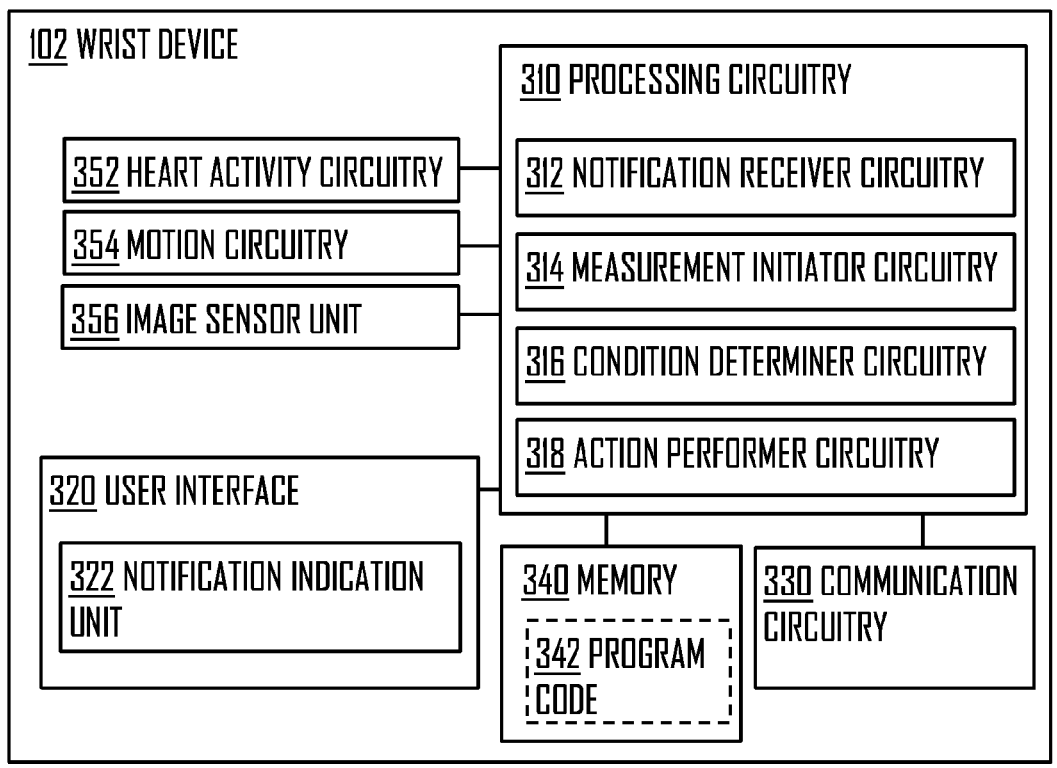
FIG. 3 illustrates a wrist device according to an embodiment of the invention.

It needs to be understood that the wrist device 102 may be used to monitor physical activity of the user 100 and/or to be used as a smart watch configured to enable communication with, for example, a portable electronic device 106, the network 110, and/or some other network, such as a cellular network. Thus, for example, the wrist device 102 may be connected (i.e. wirelessly connected) to the portable electronic device 106, such as a mobile phone, smart phone, tablet and/or computer to name a few. This may enable data transfer between the wrist device 102 and the portable electronic device 106. The data transfer may be based on Bluetooth protocol, for example. Other wireless communication methods, such as Wireless Local Area Network (WLAN) may also be used. Thus, the wrist device 102 may comprise a communication circuitry 330, as shown in FIG. 3, capable of operating with said technologies.

The wrist device 102 may receive data from the portable electronic device 106 relating to notifications obtained by the portable electronic device 106. For example, a notification of an incoming call to the portable electronic device 106 may be displayed on the wrist device 102. The notifications may comprise call notifications, text message notifications, social media notifications, software or application notifications, game notifications, to name a few examples. Virtually any notification that may be obtained and/or received by the portable electronic device 106 may be displayed on the wrist device 102. The notifications received by the wrist device 102 may comprise text, images, videos and/or sound, for example. However, the wrist device 102 may indicate the received notifications depending on the wrist device 102 configuration. Therefore, the wrist device 102 may decide how to use the received data about the notifications.

In case of communicating directly with the cellular network, the wrist device 102 may comprise similar communication capabilities as mobile devices, such as 2G, 3G, LTE, LTE-A, 4G and/or 5G communication capabilities. Thus, for example, the wrist device 102 may comprise the communication circuitry 330 capable of operating on said technologies, a Subscriber Identification Module (SIM) and/or a memory comprising a virtual SIM configured to provide a secured identification for the wrist device 102 when operating in the cellular network. Therefore, it may be possible to use the wrist device 102 to communicate directly with the cellular network. That is, receive and/or transmit phone calls, text messages, and/or data, for example. The data may be related to, for example, applications used with the wrist device 102, such as social media applications and/or training applications, for example. Therefore, the wrist device 102 may be capable of receiving notifications of events directly from the cellular network.

The wrist device 102 may be used to monitor activity and/or inactivity of the user 100. The wrist device 102 may comprise a heart activity circuitry 352 as shown in FIG. 3. The heart activity circuitry 352 may be configured to determine heart activity of the user 100, such as heart rate, Heart Beat Interval (HBI) and/or Heart Rate Variability (HRV), for example. The heart activity circuitry 352 may comprise an optical heart activity sensor, such as a PPG (photoplethysmography) sensor, configured to measure heart activity of the user 100. The optical heart activity sensor may detect the heart activity of the user 100 by optical heart rate measurement, which may comprise sending a light beam towards skin of the user 100 and measuring the bounced and/or emitted light from the skin of the user 100. The light beam may alter when travelling through veins of the user 100 and the alterations may be detected by the optical heart rate activity sensor. By using the detected data, the wrist device 102, may determine heart activity of the user 100, such as heart rate for example.

The heart activity circuitry 352 may comprise a bioimpedance sensor, wherein the bioimpedance sensor is configured to measure heart activity of the user 100. The bioimpedance measurement may be based on transmitting a radio signal into the skin of the user, and observing changes in the radio signal due to impedance changes caused by, for example, blood volume changes. Thus, heart activity of the user 100 may be determined by the wrist device 102 from the data produced by the bioimpedance sensor.

Further, besides these types of heart activity sensors, also other types of biosignal measurement sensors may be embedded into the heart activity circuitry 352. These types include but are not limited to the following: a Laser Doppler-based blood flow sensor, a magnetic blood flow sensor, an Electromechanical Film (EMFi) pulse sensor, a polarization blood flow sensor, an Electrocardiography (EKG) sensor comprising at least one electrode.

It also needs to be noted that the heart activity circuitry 352 may produce raw measurement data of the heart activity and/or it may process the measurement data into heart activity information, such as heart rate for example. The sensor(s) in the heart activity circuitry 352 may comprise data processing capabilities. Further, the raw measurement data and/or processed information may be processed by the wrist device 102 and/or transmitted to an external device, such as the portable electronic device 106.

The wrist device 102 may comprise a motion circuitry 354 as shown in FIG. 3. The motion circuitry 352 may be configured to measure motion induced by the user 100 to the wrist device 102 by moving hand (or other body parts to which the wrist device is attached to) in which the user 100 wears the wrist device 102. The motion circuitry may use other motion data, such as location data of the user, to determine motion of the user 100. For example, the motion circuitry may comprise a GPS receiver for receiving GPS data. The GPS data may be used, by the wrist device, to determine motion of the user 100.

In an embodiment, the motion circuitry 354 comprises at least one of the following: an accelerometer, a magnetometer, and a gyroscope.

In an embodiment, the motion circuitry 354 comprises an accelerometer and a gyroscope. The motion circuitry 354 may further comprise sensor fusion software for combining the accelerometer data and gyroscope data so as to provide physical quantities, such as acceleration data, velocity data, or limb trajectory data in a reference coordinate system having orientation defined by a predetermined gyroscope orientation.

In an embodiment, the motion circuitry 354 comprises a gyroscope and a magnetometer. The motion circuitry 354 may further comprise sensor fusion software to combine gyroscope data and magnetometer data so as to provide a reference coordinate system for the gyroscope based on the Earth magnetic field measured by the magnetometer. In general, the sensor fusion software described above may combine measurement data acquired from at least two motion sensors such that measurement data acquired from one motion sensor is used to establish the reference coordinate system for the measurement data acquired from at least one other motion sensor.

Still referring to FIG. 1, the heart activity measurement system may further comprise the external sensor device(s) 104 used by the user 100. The external sensor device(s) 104 may be worn by the user 100. The external sensor device(s) 104 may comprise sensors, such as a heart rate transmitter, heart rate sensor, a stride sensor, a positioning sensor, a cadence sensor and a power sensor, to mention a few. The heart rate transmitter may comprise at least one electrical, optical and/or bioimpedance sensor to measure heart activity of the user 100. The electrical sensor(s) may be, for example, based on EKG measurement. The positioning sensor may comprise a GPS, a magnetometer and/or a Bluetooth sensor. Thus, the positioning may be based on, for example, GPS location and/or Bluetooth location. The magnetometer may provide direction data based on magnetic fields on earth and/or inside structures.

The external sensor device(s) 104 may comprise a head sensor, wherein the head sensor may be configured to measure heart activity of the user 100. The head sensor may be, for example, an ear sensor which may be placed in physical connection with an ear and/or ears of the user 100. The placement may be similar to placing earplug headphones, for example. Another example may be to use a clip mechanism and/or glue-like material for the physical connection. The head sensor may utilize optical measurement and/or bioimpendace measurement for the heart rate measurement, for example. In an embodiment, the ear sensor is an in-ear sensor.

In an embodiment, the head sensor is comprised in glasses. In such case the head sensor may be comprised in earpiece(s) of the glasses, for example.

In an embodiment, the head sensor is comprised in headphones and/or earphones.

The external sensor device(s) 104 may transmit the sensor data to the wrist device 102, to the portable electronic device 106 and/or to a server 114, residing in a network 110, of the heart activity measurement system. The wrist device 102, the portable electronic device 106 and/or the server 114 may receive the sensor data. Similarly, the wrist device 102 may transmit the heart activity data, provided by the heart activity circuitry 352, the motion sensor data, provided by the motion circuitry 354, and/or some other data to the portable electronic device 106 and/or the server 114. The wrist device 102, the portable electronic device 106 and/or the server 114 may comprise at least one processor configured to process the received external sensor data, the heart activity data and/or the motion data into a set of metrics describing physical activity of the user, such as heart rate, energy expenditure and/or travelled distance, for example.

The external sensor device(s) 104, the wrist device 102, the portable electronic device 106 and/or the server 114 may each further comprise a communication circuitry, such as wireless communication circuitry, configured to enable sensor data transfer between the external sensor device(s) 104, wrist device 102, portable electronic device 106 and/or the server 114. The communication circuitry 330 comprised in the wrist device 102 may be shown in FIG. 3 as described above.

Further, the wrist device 102 and/or the portable electronic device 106 may comprise a memory, wherein the memory may be used by the devices to store the data from different sensor device(s). The memory 340 comprised in the wrist device 102 may be shown in FIG. 3. The server 114 may use a database 112, such as a training database, to store the said data. The database 112 may reside in the network 110.

In an embodiment, the external sensor device(s) 104 are comprised in the wrist device 102.

In an embodiment, the wrist device 102 comprises at least one of the following sensors: a temperature sensor, a positioning sensor and a pressure sensor. The positioning sensor may utilize GPS and/or Bluetooth information for locating the user 100. Further, the positioning sensor may comprise a magnetometer. Thus, the positioning sensor may be comprised in the motion circuitry 354, for example.

As described, the wrist device 102 may be used to receive notifications related to events, such as phone calls, from the cellular network and/or from external device(s), such as the portable electronic device 106. This may be beneficial, as these notifications may be indicated to the user 100. The indication may be done by the wrist device 102 and/or the portable electronic device 106, for example.

In an embodiment, the notifications are indicated using the external sensor device(s) 104. In such case, the wrist device 102 and/or the portable electronic device 106 may transmit the notification to the external sensor device(s) 104, wherein the external sensor device(s) 104 may receive the notification and indicate it to the user by using, for example, haptic, visual, and/or sound indication.

In some cases however, the indication of the notification on the wrist device 102 may be disturbing and/or unnecessary. In such cases, it may be beneficial that the indication, of the notification received by the wrist device 102 directly from the cellular network and/or from the portable electronic device 106, on the wrist device 102 may not be done at all, or the indication may be changed and/or terminated after the indication has been initiated. There is provided a solution for controlling notification indication on the wrist device 102.

The solution may enhance the usability of the wrist device 102, and may, for example, reduce amount of energy used for the indication of the notifications.

FIG. 2 illustrates a block diagram according to an embodiment of the invention. Referring to FIG. 2, in step 202, the wrist device 102 may receive a notification of an event, wherein the notification is indicated to the user 100 of the wrist device 102. As described earlier, the event may be, for example, a phone call, text message, social media message, to name a few examples. The indication of the event may be done by the wrist device 102 and/or the portable electronic device 106. Thus, for example, the portable electronic device 106 may receive a phone call and indicate it to the user 100. The portable electronic device 106 may further transmit the notification about the phone call to the wrist device 102. The wrist device 102 may then decide whether to indicate the notification to the user 100 or not. Therefore, the phone call may be indicated by the portable electronic device 106 and the wrist device 106, only by the portable electronic device 106, or only by the wrist device 102 in a case where the portable electronic device 106 does not indicate the phone call to the user 100. The indication may depend on the configuration of the device(s). In an embodiment, the phone call, or similar event, is not indicated at all, if the device(s) have been configured and/or set to a state where phone calls are not wanted to be received by the user 100.

In step 204, in response to receiving the notification, the wrist device 102 may initiate at least one measurement. The at least one measurement may be initiated on the wrist device 102, for example. The wrist device 102 may also transmit control message(s) to the external sensor device(s) 104, wherein the control message(s) may cause the external sensor device(s) 104 to perform measurement(s). Similarly, the wrist device 102 may also transmit control message(s) to the portable electronic device 106, wherein the control message(s) may cause the portable electronic device 106 to perform measurement(s). The control message(s) may further cause the external sensor device(s) and/or the portable electronic device 106 to transmit results of the measurement(s) to the wrist device 102.

As said, the at least one measurement may be initiated on the wrist device 102, for example. The at least one measurement may comprise measurement(s) performed by the heart activity circuitry 352, the motion circuitry 354, communication circuitry 330, and/or the image sensor unit 356 shown in FIG. 3. For example, the motion circuitry 354 may be used to detect a gesture performed by the user 100, such as acceleration of the wrist device 102. Other examples may include using the image sensor unit 356 to detect face of the user 100. These may be discussed later in more detail.

In step 206, the wrist device 102 may determine, based on the at least one measurement, that a predetermined condition is met. This may mean, for example, that the user 100 has performed some action(s) that may have been detected using the at least one measurement. For example, if the user 100 lifts the wrist device 102 in order to view the information on the wrist device (e.g. the indication of the notification), the measurement(s) performed by the motion circuitry 354 may detect the lifting using, for example, accelerometer and/or gyroscope. The wrist device 102 may then determine, based on the data from the motion circuitry 354 that the user 100 has lifted his/her arm, and thus determine that the predetermined condition has been met. Naturally, other measurement(s) may be used to determine similar action, such as image sensor unit 356 data may be used to determine that the user is viewing the wrist device 102, for example.

Also, for example, it may be possible to determine, using data from the communication circuitry 330 that a signal received from the portable electronic device 106, by the wrist device 102, is of certain strength or over a certain threshold. This may mean that the portable electronic device 106 is close to the wrist device 106, such as in a hand of the user 100, for example.

In step 208, in response to the determining that the predetermined condition is met, the wrist device 102 may perform an action having an effect on the indication of the notification. This may mean that the indication is, for example, terminated or changed. For example, if the wrist device 102 receives a notification of a phone call, the notification may be indicated to the user 100 by a haptic indication, such as vibration, on the wrist device 102. The wrist device 102 may then determine that the user 100 lifts the wrist device 102 in order to view the notification, and thus the haptic indication may be stopped. It may also be possible that the wrist device 102 decides not to use, for example, the haptic indication, if the wrist device 102 is determined to be viewed by the user 100 at the time of receiving the notification. For example, visual indication may be determined to be enough, by the wrist device 102, if the user 100 lifts the wrist device 102 to view the notification and/or is already viewing the wrist device 102 when the notification is received.

In an embodiment, the steps shown in FIG. 2 are performed by a computing device, such as the portable electronic device 106. Thus, for example, the computing device may obtain notification of an event, initiate the at least one measurement on the computing device, the wrist device 102 and/or on the external sensor device(s) 104, determine that the predetermined condition is met, and perform an action on the indication of the notification. In such case, the notification may be initially indicated, and then the indication may be changed as shown in step 208. It may also be possible that the notification is indicated based on the result of the at least one measurement.

In an embodiment, the indication of the notification is performed based on the result of the at least one measurement. For example, the wrist device 102 may first obtain the notification. The notification may have been indicated by the portable electronic device 106, if the notification is received from the portable electronic device 106. The wrist device 102 may then perform steps 204, 206 accordingly. In step 206, the predetermined condition may be that the wrist device 102 is not yet viewed by the user 100, for example. Thus, in step 208, the wrist device 102 may indicate the notification, for example, on the wrist device 102. The indication in such case may comprise, for example, haptic indication, visual indication and/or sound indication.

Further, the wrist device 102 may then determine that the wrist device 102 is viewed by the user 100. The determination may be based on similar measurement(s) as in step 204, for example. In response to the determining, the wrist device 102 may perform a second action having an effect on the indication of the notification. This may mean, for example, terminating at least one of the haptic, visual and/or sound indication.

Let us now look closer on the wrist device 102 by looking at an embodiment with reference to FIG. 3. Referring to FIG. 3, the wrist device 102 may comprise the heart activity circuitry 352, motion circuitry 354, the image sensor unit 356, processing circuitry 310, user interface 320, communication circuitry 330 and/or memory 340.

The processing circuitry 310 may comprise a notification receiver circuitry 312 configured to receive the notification of the event, wherein the notification is indicated to the user 100 of the wrist device 102; a measurement initiator circuitry 314 configured to, in response to receiving the notification, initiating the at least one measurement; a condition determiner circuitry 316 configured to determine, based on the at least one measurement, that the predetermined condition is met; and an action performer circuitry 318 configured to, in response to the determining that the predetermined condition is met, perform the action having the effect on the indication of the notification.

In an embodiment, the processing circuitry comprises at least one processor, wherein the at least one processor and the at least one memory 340 including a computer program code 342, wherein the at least one memory 340 and the computer program code 342 are configured, with the at least one processor, to cause the wrist device 102 to perform at least the operations described in relation to steps 202 to 208.

In an embodiment, the wrist device comprises the at least one processor, wherein the at least one processor and the at least one memory 340 including a computer program code 342, wherein the at least one memory 340 and the computer program code 342 are configured, with the at least one processor, to cause the wrist device 102 to perform the operations described in relation to steps 202 to 208, and embodiments described above and/or hereinafter.

The user interface 320 may enable the user 100 to interact with the wrist device 102. The user interface 320 may comprise one or more button, such as physical button(s), a touch-screen display, microphone, keypad, a speaker, one or more displays, at least one light source (i.e. light emitting diode) a haptic member to name a few examples. The haptic member may comprise, for example, a vibrating element and/or electrical shock member, wherein the electrical shock member may be configured to produce electrical shocks to the skin of the user 100. These electrical shocks may be minimal, and thus harmless to the user 100. However, these minimal electrical shocks may be of such proportions that the sense of touch of the user 100 may be able to detect the electrical shocks.

The user interface 320 may comprise a notification indication unit 322. The notification indication unit 322 may enable the wrist device 102 to indicate the received notification to the user 100. The notification indication unit 322 may comprise a haptic member, a display, at least one light source, such as light emitting diode (LED), and/or sound producing member, for example. It may also be possible that the notification indication unit 322 causes the user interface 320 to indicate the notification to the user 100.

The notification indication unit 322 may be configured to indicate the notification to the user 100 of the wrist device 102 by the haptic indication, the sound indication, and/or the visual indication. As described earlier, the wrist device 102 may, for example, first indicate the notification using all three indication methods, and after determining that the predetermined condition is met, use only, for example, visual indication. In another example, the wrist device 102 may first not indicate the received notification. After determining that the predetermined condition is met, the wrist device 102 may use at least one of the three indication methods.

The communication circuitry 330 may be configured to enable the wrist device 102 to communicate with the portable electronic device 106, the external sensor device(s) 104, the cellular network, the network 110 and/or some other external device. The cellular network may be comprised in the network 110, wherein the network 110 may be accessible by using cellular data, wireless (i.e. WLAN) and/or wired data connection. Thus, the communication circuitry 330 may be capable of operating on, for example, Bluetooth, Bluetooth Low Energy (BLE), WLAN, cellular (i.e. 2G, 3G, LTE, LTE-A, 4G, 5G), Near Field Communication (NFC) technologies, to name a few examples. However, the capabilities of the communication circuitry 330 may not be limited to these examples.

In an embodiment, the performing the action, by the wrist device 102, having the effect on the indication of the notification comprises terminating at least one of the haptic indication, the sound indication, visual indication of the notification. This may happen after the wrist device 102 determines that the predetermined condition is met. The other way around, the wrist device 102 may start or initiate at least one of the haptic indication, the sound indication, visual indication of the notification, after the predetermined condition is met. For example, the wrist device 102 may first indicate the notification using haptic and/or sound indication, and after determining that the predetermined condition is met, initiate visual indication of the notification. This may be beneficial, for example, for a text message, wherein the content of the text message may be indicated to the user 100 when the user 100 views the wrist device 102. This may save energy and enhance user experience as the visual indication may be configured to last for a certain time, and thus this way it may be ensured that the user 100 may be able to view content of the text message or some other notification.

In an embodiment, the predetermined condition triggers the wrist device 102 to visually indicate the notification to the user 100. Thus, for example, twitter message may be first indicated using haptic and/or sound indication, and after the predetermined condition is met, visually indicate the twitter message to the user 100.

Figure 4A:
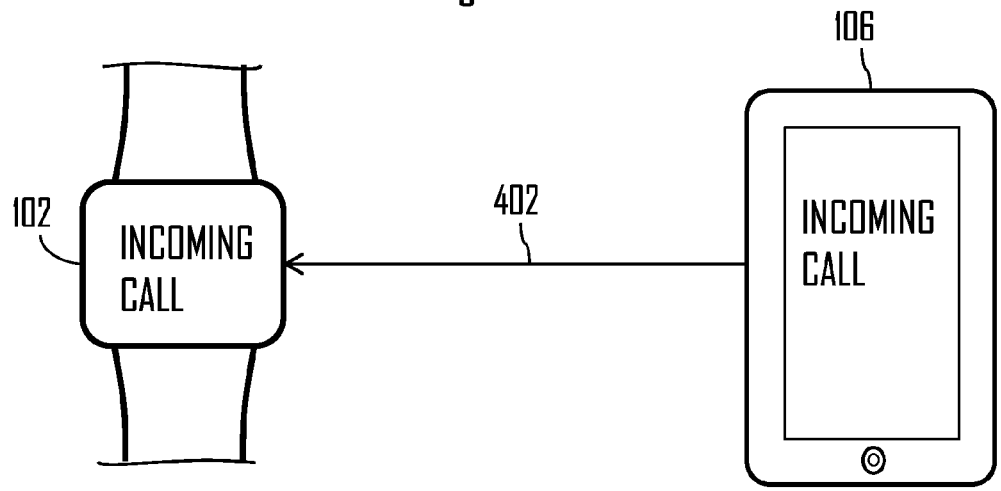
FIGS. 4A to 4B illustrate some embodiments of the invention.

FIG. 4A illustrates an embodiment of the invention. Referring to FIG. 4A, the wrist device 102 may receive a notification 402 of an event, such as incoming call, from the portable electronic device 106. As shown in FIG. 4A, the incoming call may be indicated by the wrist device 102 and/or the portable electronic device 106. The visual indication may comprise information about the event, such as the type of the event. In this example, the type of the event may be incoming call. The visual indication may comprise content of the notification, such as text message content, or at least a part of the content. The visual indication may comprise context of the notification, such as caller and/or message sender's id and/or number, social media pseudonym, conversation group (i.e. hashtag or similar), to name a few examples. Further, the visual indication may comprise a possibility to interact with the event of which the notification was received.

For example, the visual indication may comprise possibility to reject and answer an incoming call. If the incoming call is received by the portable electronic device 106, the wrist device 102 may transmit a control message to the portable electronic device 106 to answer and/or reject the call. This may be beneficial, for example, if headphones or similar are used with the portable electronic device 106, as then the user 100 may control at least some the notification related actions on the wrist device 102 without bothering to answer and/or reject the call from the portable electronic device 106.

In an embodiment, wrist device 102 receives the notification from the external sensor device(s) 104. The notification may be related to, for example, exercise-related data, such as exceeding of heart rate limit, information about remaining time of the exercise, information about exceeding a calorie limit, exceeding of predetermined time limit, to name a few examples. It may be beneficial to, for example, first indicate the notification from the external sensor device(s) 104, and stop the indication after it has been determined that the user has seen the indication content.

In an embodiment, the visual indication of the notification lasts for a predetermined time after the wrist device 102 determines that the predetermined condition has been met. This may provide the user 100 enough time to view the content of the notification, for example. The time may be, for example, 5 seconds or more 10 seconds or more, 15 seconds or more, to name a few examples.

In an embodiment, the portable electronic device 106 comprises at least one of the described external sensor device(s) 104.

Figure 4B:
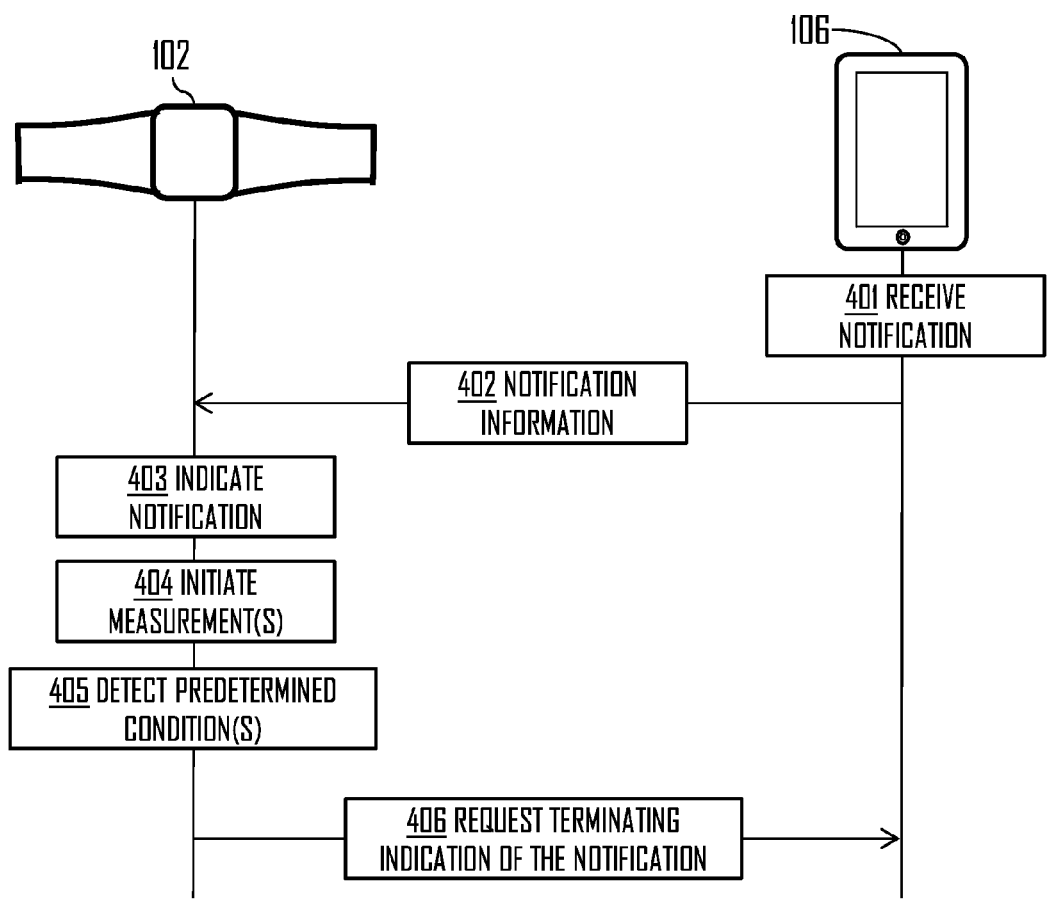

FIG. 4B illustrates a flow diagram according to an embodiment of the invention. Referring to FIG. 4B, the portable electronic device 106 may receive a notification (step 401). The portable electronic device 106 may transmit the notification and/or notification information to the wrist device 102 (step 402). The notification information may comprise at least some information about the received notification. The wrist device 102 may receive the notification as described above. The wrist device 102 may then indicate the notification to the user 100 (step 403) and initiate the at least one measurement (step 404). Based on the measurement(s), the wrist device 102 may detect that at least one predetermined condition is met (step 405).

In an embodiment, the performing the action having the effect on the indication of the notification comprises transmitting a control message (step 406), by the wrist device 102, to the portable electronic device 106, wherein the control message causes the portable electronic device 106 to terminate a haptic indication, a sound indication and/or a visual indication of the notification on the portable electronic device 106. Thus, the wrist device 102 may control, at least partially, the indication of the notification by the portable electronic device 106.

For example, an incoming call is indicated by the portable electronic device 106. The wrist device 102 may receive the notification, as shown in step 402, and determine that the user 100 is viewing the wrist device 102. Therefore, the indication on the portable electronic device 106 may be determined to be unnecessary, and the control message to cause terminating the indication may be transmitted, by the wrist device 106, to the portable electronic device 106.

Figure 5A:
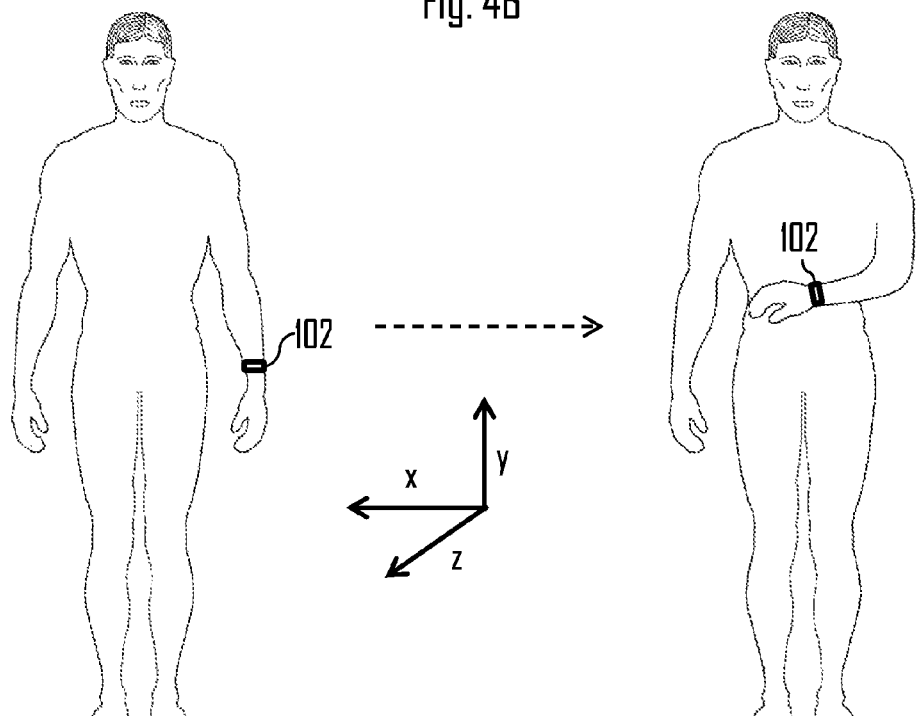
FIGS. 5A to 5C illustrate some embodiments of the invention.
Figure 5B:
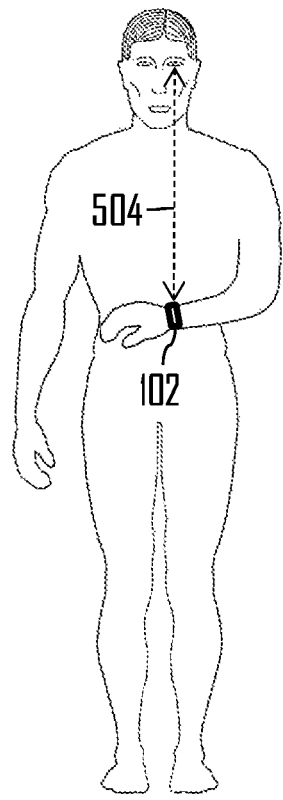
Figure 5C:
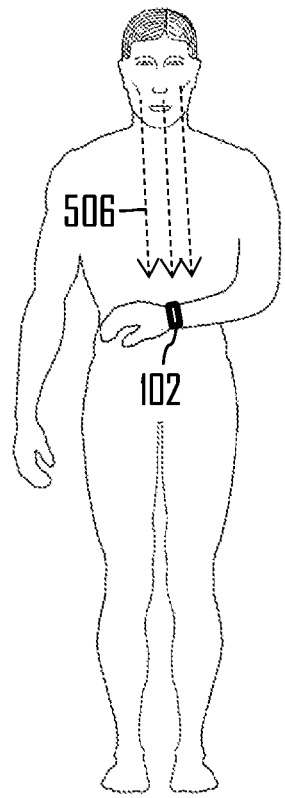

FIGS. 5A to 5C illustrate some embodiments. As described above, the determination of the predetermined condition may be based on the at least one measurement performed by the wrist device 102, the external sensor device(s) 104 and/or the portable electronic device 106. The at least one measurement may comprise at least one measurement performed by the motion circuitry 354, or more particularly, by at least one motion sensor comprised in the motion circuitry 354; at least one measurement performed by the heart activity circuitry 352; at least one measurement performed by the image sensor unit 356; and/or at least one measurement performed based on data and/or information obtained from the communication circuitry 330.

Referring to FIG. 5A, an example of using the motion circuitry 354 for the measurement is shown. Let us imagine that a notification is received by the wrist device 102. The list of predetermined condition(s) in order to take action concerning the indication of the notification may comprise a predetermined condition, wherein the predetermined condition is that the user 100 is viewing the wrist device 102. In the example of FIG. 5A, the determination that said predetermined condition is met, may be based on measurement(s) by the motion circuitry 354.

Still referring to FIG. 5A, the determining that the predetermined condition is met may comprise detecting a gesture performed by the user 100 of the wrist device 102. The gesture may be, in the example of FIG. 5A, that the user lifts and rotates his or her arm in order to view the wrist device 102. At least one of the lifting and the rotating may be detected by the motion circuitry 354 by using, for example, at least one acceleration sensor and/or at least one gyroscope. The motion circuitry 354 may be able to detect three-dimensional (x, y, z) acceleration of the wrist device 102. Naturally, there may more than one gesture that may be detected by the motion circuitry 354, or by the wrist device 102 based on the data from the motion circuitry 354. Each detected gesture may have a different effect on the indication of the notification. For example, if the user 100 shakes his or her arm, the indication of the notification may be terminated totally, whereas the notification may be visually indicated to the user 100 when the wrist device 102 is viewed. There may a number of different gestures. One may that that the user 100 reaches for his or her portable electronic device 106. This may be detected, for example, using acceleration sensor(s) to detect that hand movement is towards pocket of the user 100.

In an embodiment, the gesture detection comprises detecting, by the wrist device 102, that the user 100 lifts and rotates an arm to which the wrist device 102 is attached to, wherein the determining of the arm lift and rotation is based on the measurement by the motion circuitry 354.

Referring to FIGS. 5B and 5C, the image sensor unit 356 may be used to perform measurement(s), wherein the wrist device 102 may determine whether the predetermined condition is met based on the data from said measurement(s). The gesture detection may comprise detecting a face of the user 100, wherein the face detection may be enabled by the image sensor unit 356. In such case, the gesture may be that the user views his or her wrist device 102, and the detection of such gesture may be based on the face detection.

The face detection may at least partly be based on, for example, detecting a heat signal 506 from the face of the user 100, wherein the image sensor unit 356 may comprise an infrared sensor to detect the heat signal 506. As the user 100 may be wearing clothes insulating and/or reducing amount of given out heat by a body tissue of the user 100, the face may be a part from which given out heat 506 may be detected. Further, the wrist device 102 may detect increase in the heat signal 506 after receiving the notification, and deduce that the wrist device 102 may be viewed by the user 100. Naturally, there may be other heat sources that may be detected by the infrared sensor. However, when the wrist device 102 is at a certain distance from the face of the user 100, the heat signal 506 may be between certain limits, and thus the determination may be based on that the heat signal 506 is of certain strength.

Looking at the example of FIG. 5B, the image sensor unit 356 may comprise an image sensor, such as a camera, a matrix sensor and/or a photodiode, wherein the face detection may comprise detecting at least one facial feature 504 of the user 100 and/or light emitted from the face of the user 100. The facial feature 504 may be, for example, eye detail; distance between eyes; and/or silhouette of the face, and/or a part of the face.

In an embodiment, the individual user 100 is recognized using the image sensor. The recognizing may be based, for example, on comparing eye detail(s), and/or silhouette of the face and/or a part of the face. Thus, content of the notification may be displayed for the specific user 100, and not to some other user using the wrist device 102.

In an embodiment, the gesture detection comprises: detecting that the user lifts and rotates the arm to which the wrist device 102 is attached to, and in response to the detecting, initiating the face detection measurement by the image sensor unit 356. This may further enhance effectiveness and/or reliability of the determination that the user 100 is viewing the wrist device 102 after receiving the notification.

Figure 6A:
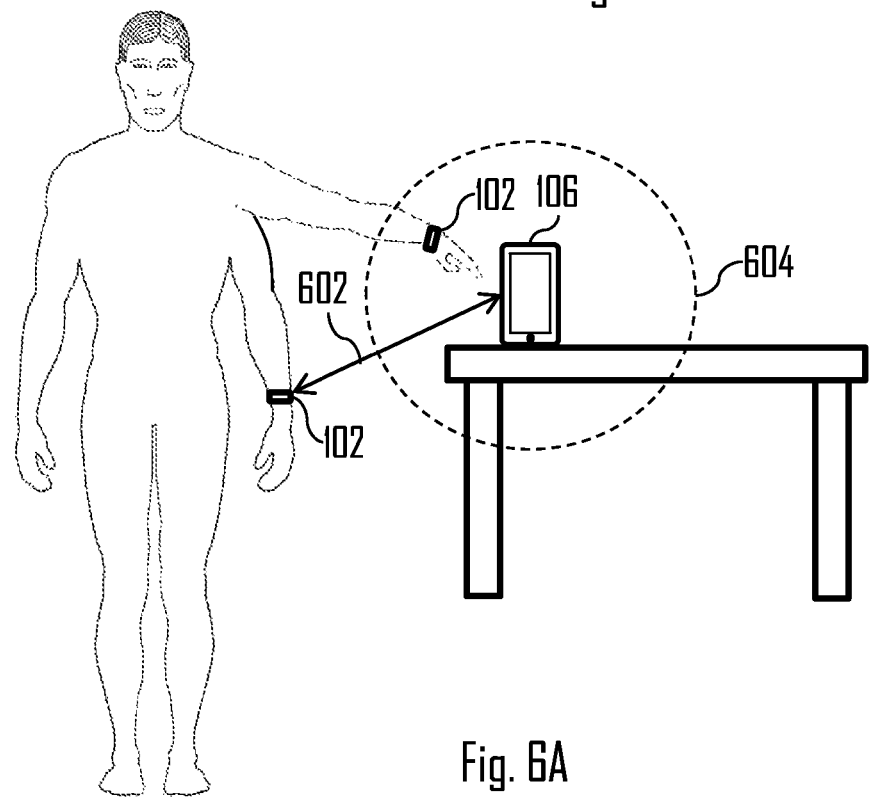
FIGS. 6A to 6C illustrate some embodiments of the invention.
Figure 6B:
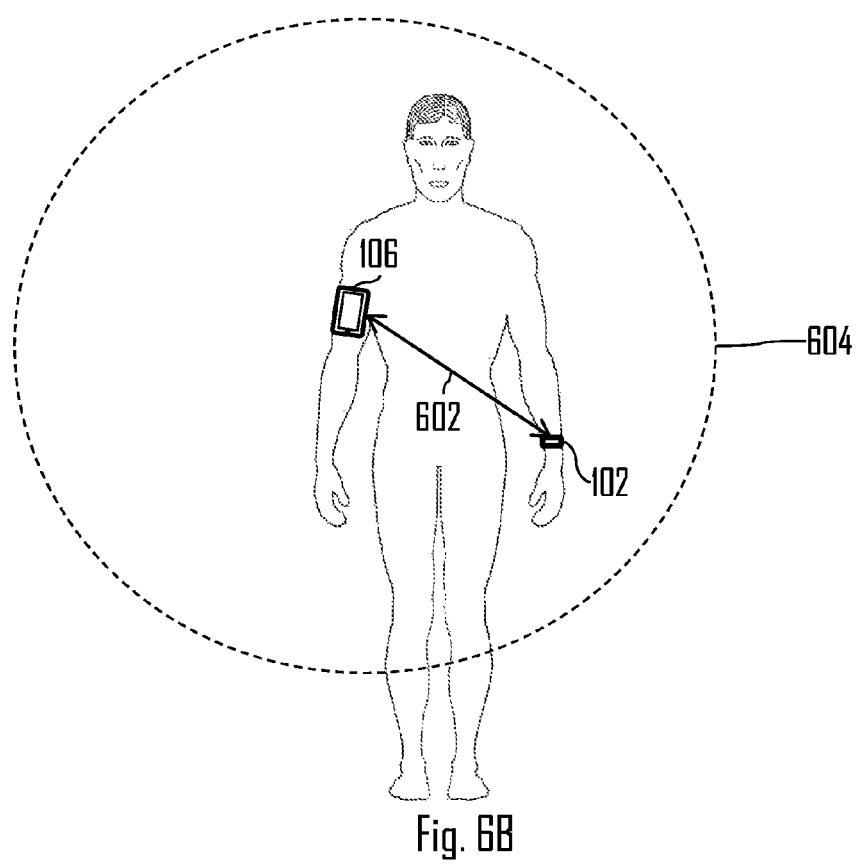
Figure 6C:
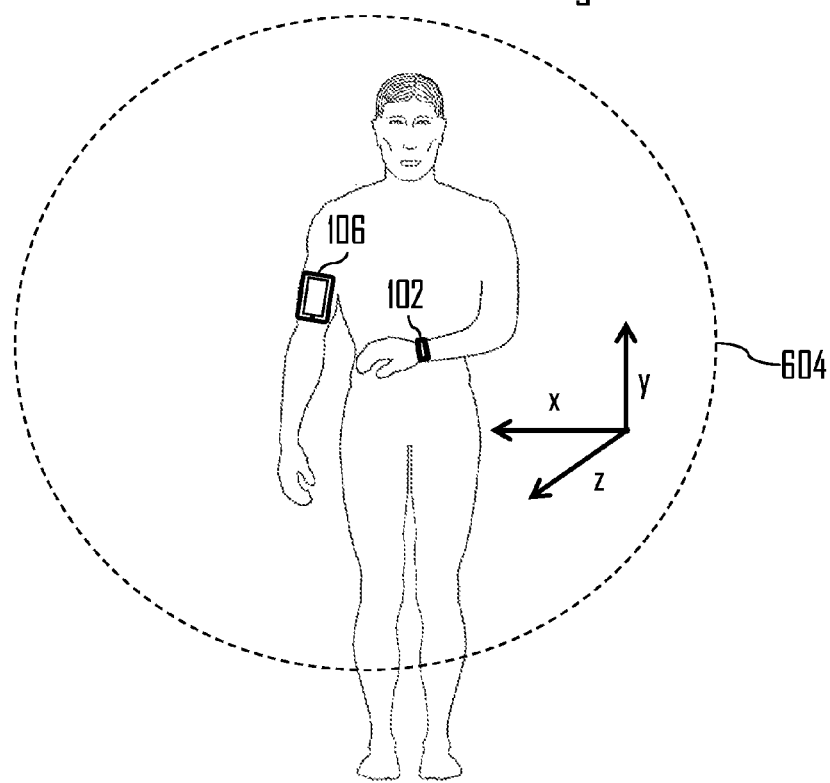

FIGS. 6A to 6C illustrate some embodiments of the invention. Referring to FIG. 6A, the determining, by the wrist device 102, that the predetermined condition is met may comprise determining that a detected signal strength, by the wrist device 102, of a transmission, by the portable electronic device 106, is under a threshold, and determining that the detected signal strength of the transmission increases over the threshold. In FIG. 6A, the threshold may be exceeded, for example, when the wrist device 102 is within the circle 604.

The signal strength determination, by the wrist device 106, may be based on the signal strength of a communication link 602 between the wrist device 102 and the portable electronic device 106, for example. The communication link 602 may be based on Bluetooth, for example, wherein Received Signal Strength Indicator (RSSI) may be used for the determination. Thus, when the RSSI reaches over a certain threshold, the wrist device 102 may determine that the wrist device 102 is within the circle 604, and perform an action concerning the indication of the notification, such as silencing the wrist device 102 and/or terminating haptic indication. The communication link 602 may be used to transmit the notification to the wrist device 102, but it may also be used to transfer different data between the portable electronic device 106 and the wrist device 102.

It may be also possible to use NFC connection and/or similar proximity detection technologies, such as Radio Frequency Identification (RFID), to determine that the predetermined condition is met. In such example, the threshold may be zero, meaning that the predetermined condition may be met when the NFC transmission or advertising, by the portable electronic device 106 is detected, by the wrist device 102, and/or when the NFC connection between the wrist device 102 and the portable electronic device 106 is established, after first not detecting the NFC transmission by the portable electronic device 106 when the at least one measurement is initiated.

To put it in other words, the determining, by the wrist device 102, that the predetermined condition is met may comprise determining that a detected signal strength, by the wrist device 102, of a transmission, by the portable electronic device 106, is zero, and then determining that the detected signal strength of the transmission increases over zero. Thus, first no transmission is detected, and after some time transmission by the portable electronic device 106 is detected.

In an embodiment, the wrist device 102 comprises a proximity sensor configured to detect proximity of the portable electronic device 106. Thus, the determination that the predetermined condition is met may be based on the detection by the proximity sensor.

In an embodiment, the wrist device 102 may detect sound and/or vibration produced by the portable electronic device 106, and determine proximity of the portable electronic device 106 based on the amplitude of the sound and/or vibration.

Referring to FIG. 6B, the determining that the predetermined condition is may comprise, determining, by the wrist device 102, that the detected signal strength, by the wrist device 102, of the transmission, by the portable electronic device 106, is over the threshold. This may happen, for example, if the portable electronic device 106 is in the hand of the user 100 and/or attached to the user 100 when the at least one measurement is initiated. The described scenario may differ from the example of FIG. 6A in that, when the at least one measurement is initiated, the detected signal strength may already be over the threshold, whereas in the example of FIG. 6A the detected signal strength may be first under the threshold.

It may be possible to determine, for example, RSSI of the transmission which is used to transfer the notification. It may be equally possible to initiate proximity detection after receiving the notification, wherein the proximity detection may be based on, for example, NFC, sound amplitude and/or vibration amplitude.

In an embodiment, the portable electronic device 106 broadcasts advertising data using, for example, BLE protocol. The wrist device 102 may determine the proximity of the portable electronic device 106 from the RSSI of the received advertising signal used to broadcast the advertising data. For example, active scanning may be used by the wrist device 102, which may be activated as a part of the at least one measurement. Similarly, the NFC may be activated on the wrist device 102 as a part of the at least one measurement. BLE and NFC may be used together or separately.

Referring to FIG. 6C, the determining that the predetermined condition is met may comprise, in response to the determining, by the wrist device 102, that the detected signal strength of the transmission by the portable electronic device 106 is over the threshold, initiating the gesture detection. The gesture detection may comprise, for example, detecting that the user 100 reaches for the portable electronic device 106, wherein the detection of the reaching is based on the measurement by the motion circuitry 354. Similar gesture-based additional detection may be used, for example, in the example of FIG. 6A. This may enhance the reliability of detecting the predetermined condition.

For example, let us imagine that the user 100 is keeping his portable electronic device 106 is his or her pocket. After receiving the notification, the wrist device 102 may determine, using for example RSSI and/or NFC, that the signal strength detected by the wrist device 102 is over the threshold (i.e. RSSI is over the threshold; and/or NFC connection is established and/or available). This may suggest that the portable electronic device 106 is close to the user 100. The wrist device 102 may then initiate gesture detection to determine, for example, that the user 100 reaches for the portable electronic device 106. Thus, the indication of the notification may be changed after the gesture detection.

There may be more than one threshold that may be used. For example, there may be two or more RSSI values that may be used. For example, if RSSI of the transmission from the portable electronic device 106 detected by the wrist device 102 is over a first threshold, the wrist device 102 may take an action concerning the indication of the notification. If RSSI of the transmission from the portable electronic device 106 is over a second threshold, the wrist device 102 may, for example, activate gesture detection, wherein the gesture detection may be used to detect whether or not an action concerning the indication of the notification should be performed. Different thresholds may also be related to and/or activate different gesture detection(s), for example.

It needs to be noted that there may be a lot of different predetermined conditions that may have an effect on the indication of the notification. As described above, one predetermined condition may be that the user looks at the wrist device 102. This may be detected, for example, by the motion circuitry 354 measuring that forearm of the user 100 rises and rotates so that the user 100 may view the wrist device 102. Same predetermined condition may be detected using the image sensor unit 356. Naturally, both described measurements may be used in combination so that the measurement by the image sensor unit 356 may be initiated after the detection of the arm movement.

Further, one predetermined condition may be that the proximity, to the wrist device 102, of the portable electronic device 106 transmitting the notification, is greater than a threshold. This may be detected by the wrist device 102, for example, using RSSI, NFC, a proximity sensor, such as infrared sensor, and/or sound or vibration amplitude detection. Another predetermined condition may be that the proximity, to the wrist device 102, of the portable electronic device 106 transmitting the notification is lesser and/or equal compared to the threshold, and that the proximity increases so that it increases over the threshold. Another predetermined condition may be that the proximity, to the wrist device 102, of the portable electronic device 106 transmitting the notification, is greater than a threshold, and that the wrist device 102 determines that a gesture is performed by the user of the wrist device 102. The gesture may be, for example, looking at the wrist device 102 and/or reaching for the portable electronic device 102 by the user 100.

In an embodiment, the portable electronic device 106 detects that the user 100 is viewing the portable electronic device 106. This may happen, for example, when the notification is received by the wrist device 102. The portable electronic device 106 may then transmit a control message to the wrist device 102, wherein the wrist device 102 may receive the message and perform an action concerning the indication of the notification on the wrist device 102. For example, the wrist device 102 may stop indicating the notification, or stop at least the sound and/or haptic indication. The determination by the portable electronic device 106 may be based on, for example, facial recognition, antenna impedance changes due to touching by the hand of the user 100, touch sensor data, such as touch screen display, acceleration sensor data, to name a few example.

In an embodiment, the wrist device 102 comprises at least one attachment element to enable detachable attachment of the wrist device 102 around the wrist of the user 100. When attached to the wrist of the user 100, the gesture detection of the wrist device 102 may be activated so that the gesture detection may be started when the notification is received. If the wrist device 102 is not attached to the wrist, it may be beneficial not to activate the gesture detection and/or any other measurement, as this may require energy and thus shorten battery life, for example. Therefore, the wrist device 102 may determine, after receiving the notification, that the wrist device 102 is in use, before initiating the at least one measurement. As said, the determination may be based on the determination that the wrist device 102 is attached to the wrist of the user 100. This may be based on, for example, detecting heartbeat(s) or heart rate of the user 100 using optical and/or biometric measurement, detecting movement of the hand, wherein the movement of the hand suggest that the wrist device is used by the user 100, and/or determining changes in wrist device's 102 antenna impedance. The impedance of the antenna, used by the communication circuitry 330, for example, may change when the wrist device 102 is close to skin of the user 100, especially when the wrist device 102 may be in physical connection with the skin of the user 100.

Figure 7A:
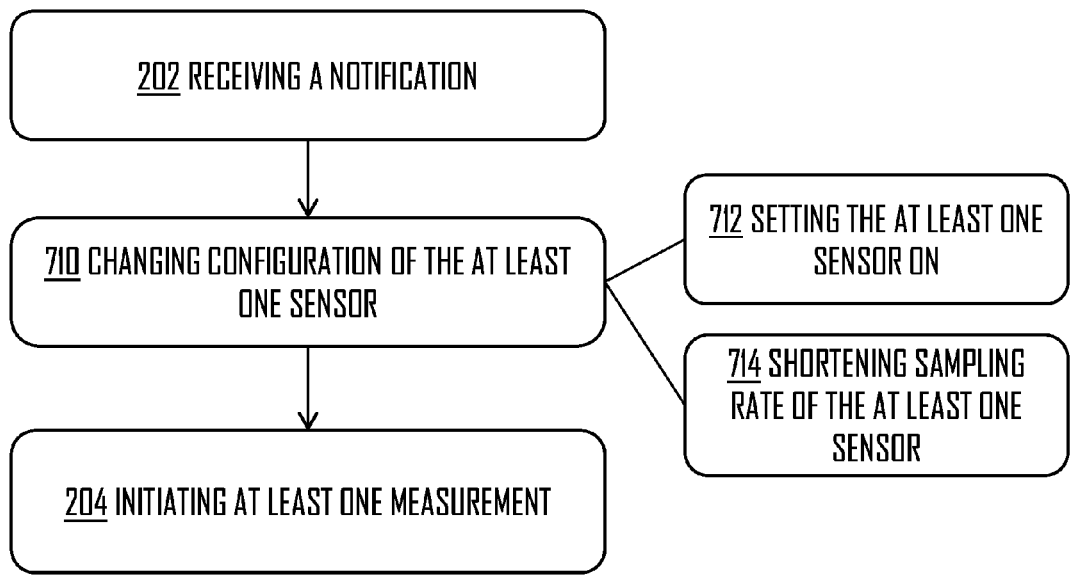
FIGS. 7A to 7D illustrate some embodiments of the invention.

Let us now look some embodiments illustrated in FIGS. 7A to 7D. Referring to FIG. 7A, the wrist device 102 may receive the notification (step 202) as described above. The at least one measurement of step 204 may be performed by at least one sensor, such as sensor(s) of the wrist device 102 (i.e. heart activity circuitry 352, motion circuitry 354, image sensor unit 356), the sensor(s) of the external sensor device(s) 104 and/or sensor(s) of the portable electronic device 106. The wrist device 102 may, in response to receiving the notification, change configuration of the at least one sensor performing the at least one measurement (step 710). This may mean that the sensor(s) performing the measurement(s) are, in such case, configured before initiating the measurement(s).

The changing the configuration of the at least one sensor, in step 710) may comprise switching the at least one sensor on (step 712), shortening sampling rate of the at least one sensor (step 714), and/or increasing sensitivity of the at least one sensor. For example, the wrist device 102 may save battery by keeping motion circuitry 354 off when it is not needed, and start it when the notification is received if the motion circuitry 354 is required for the at least one measurement.

Similarly, the sampling rate may be longer when the wrist device 102 is used, for example, to measure physical activity of the user 100 (i.e. running, swimming). When the notification is received, the sampling rate may be shortened to better detect, for example, user gestures, such as raising the wrist device 102 in order to view the wrist device 102. In one example, the user 100 is running and the GPS sensor and/or gyroscope in the motion circuitry 354 may be on, but the acceleration sensor is off. When the notification is received, the acceleration sensor may be switched on in order to detect the gesture(s) by the user. In another example, the image sensor unit 356 is switched on when the notification is received in order to initiate facial recognition.

It needs to be further noted that one or more elements of the motion circuitry 354 and/or image sensor unit 356 may be switched on and/or otherwise configured. For example, only infrared sensor of the image sensor unit 356 may be switched on. In another example, only image sensor (i.e. camera) may be switched on. Naturally, it may be possible to switch both elements (e.g. image sensor, infrared sensor) on. This feature may further enhance first detecting the gesture(s) and second save battery of the wrist device 102.

Figure 7B:
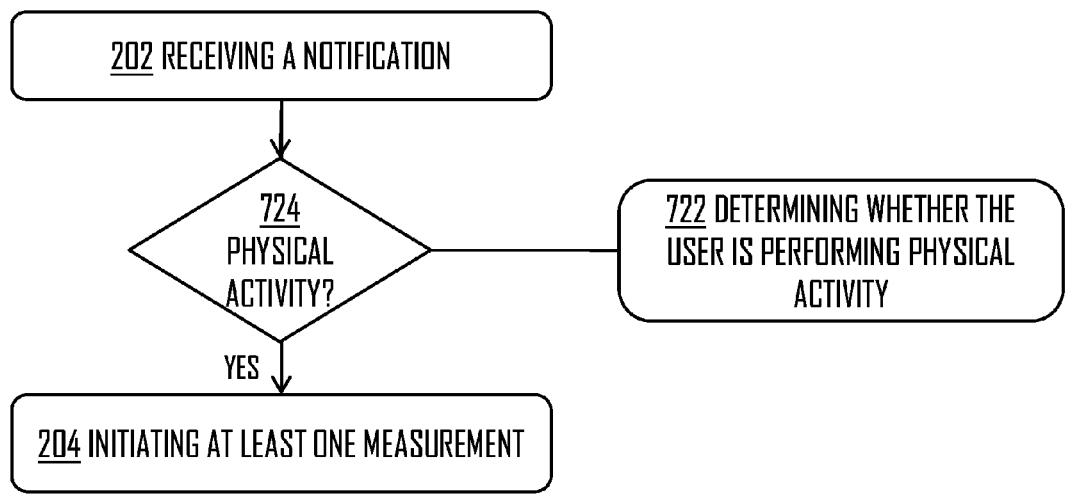

Referring to FIG. 7B, in step 722, the wrist device 102 may determine whether the user of the wrist device is performing a physical activity. For example, the wrist device 102 may use information from the heart activity circuitry 352, motion circuitry 354, image sensor unit 356 and/or the external sensor device(s) 104 for the determination. In one example, the wrist device 102 may enable the user 100 to switch wrist device 102 into exercising mode (e.g. performing physical activity). Further, sport and/or activity type may also be enabled to be set to the wrist device 102.

After receiving the notification (step 202), the wrist device 102 may determine if the user is performing the physical activity (block 724) The determination may be based on step 722. If the user is performing the physical activity, the wrist device 102 may initiate the at least one measurement (step 204) in response to receiving the notification (step 202). For example, the measurement(s) may be initiated if the user is determined to be running.

In an embodiment, the wrist device 102 determines whether the user 100 of the wrist device 102 is performing the physical activity, and if the user is performing the physical activity, cancel the initiation of the at least one measurement. For example, if the user 100 is running, the movement of the hand during running may have an effect on the measurement(s). Thus, it may be beneficial to save, for example, battery of the wrist device 102 by not initiating the measurement(s). In such case, the notification may be indicated to the user 100 normally, and he/she may take action concerning the notification (i.e. pressing accept call button on the wrist device 102). Additionally, used measurement(s) may be selected based on the activity. For example, when running it may be beneficial to use facial recognition, RSSI and/or NFC instead of using the acceleration sensor and/or gyroscope.

Figure 7C:
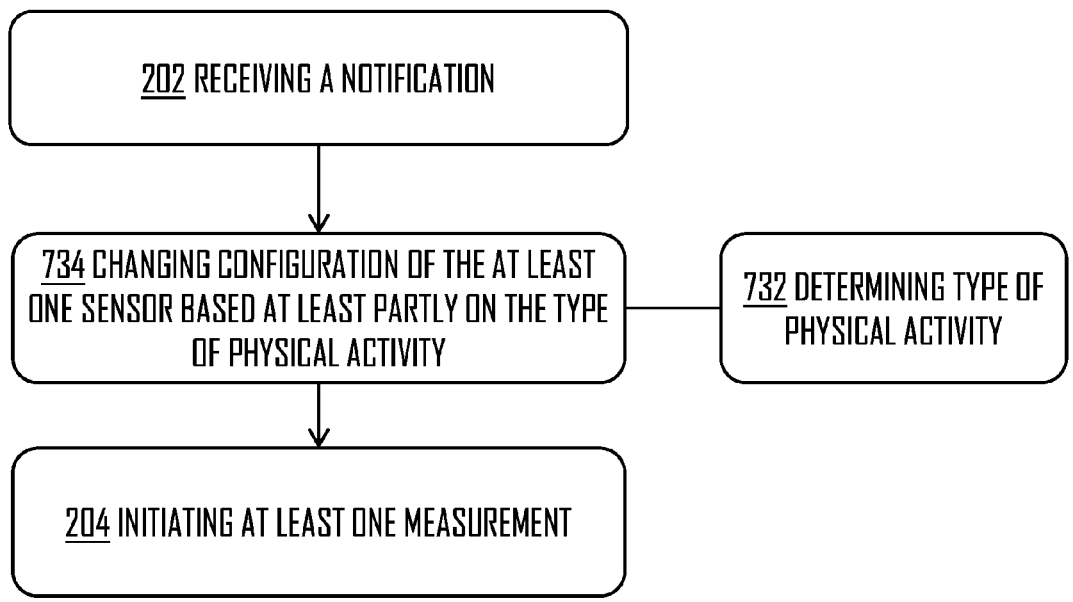

Referring to FIG. 7C, the wrist device 102 may determine the type of the physical activity performed by the user 100 (step 732). For example, the type may be determined from data of the motion circuitry 354 and/or heart activity circuitry 352. In step 734, the wrist device 102 may change the configuration of the at least one sensor, such as the heart activity circuitry 352, motion circuitry 354, image sensor unit 356, and/or the communication circuitry 330, based at least partly on the type of the physical activity when the notification is received. For example, to detect gestures by the user 100 when he/she is running, it may be beneficial to increase sampling rate in order to detect the gesture(s) and/or distinguish the gesture(s) from normal hand movement caused by the running. As mentioned above, measurement(s) may be selected based on the activity. Thus, for example, configuration of the communication circuitry 330 may be changed based on the activity.

In an embodiment, in response to receiving the notification in step 202, the wrist device 102 changes configuration of the communication circuitry 330. This may mean a number of things. For example, the RSSI measurement and/or NFC measurement may be initiated. Thus, for example, NFC and/or Bluetooth circuitries may be switched on. It may also be possible that sensitivity of the communication circuitry 330 is changed (i.e. the sensitivity is increased). As in step 734, the configuration of the communication circuitry 330 may be changed based on the type of the physical activity. Further, configuration of the communication circuitry 330 may be performed before initiating the measurement(s) by the communication circuitry 330.

Figure 7D:
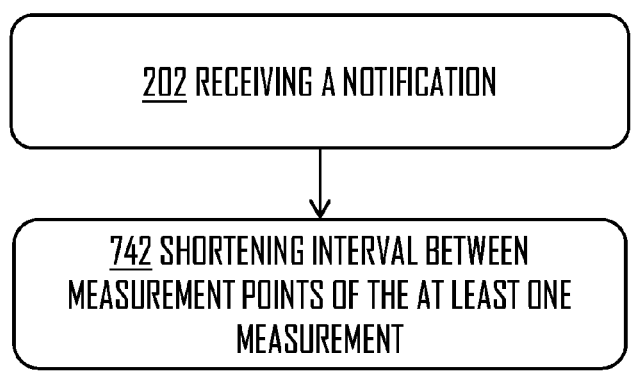

Referring to FIG. 7D, after receiving the notification (step 202), the wrist device 102 may shorten time interval between measurement points of the at least one measurement. For example, the RSSI measurement may comprise measured values that are obtained from the measurement points respectively. Thus, the wrist device 102 may perform the RSSI measurement more intensely when the time interval is shortened.

Shortening may be performed in response to receiving the notification, for example. For example, the wrist device 102 may use the information from the communication circuitry 330 for the RSSI measurement. It may be beneficial to perform the RSSI measurement such that the time interval between the measurement points is shortened at some time after receiving the notification. It may be possible, for example, that the time interval is X at the beginning of the RSSI measurement, and after some predetermined time the wrist device 102 shortens the time interval to Y, wherein Y is smaller than X. For example, X may be 100 milliseconds and Y may be 10 milliseconds. Therefore, the shortening may be performed before and/or during the measurement(s).

Similarly, for example, the time interval between measurement points of the gesture detection (i.e. image sensor unit 356, motion circuitry 354) may be shortened.

In an embodiment, the time interval of between the measurement points is increased in after some predetermined time. For example, after the predetermined time the time interval may be beneficial to make longer in order to save battery.

In an embodiment, in response to receiving the notification of an event, the wrist device 102 transmits a control message to the portable electronic device 106, wherein the control message causes the portable electronic device 106 to change configuration of its communication circuitry. For example, time interval between Bluetooth advertisement packets transmitted by the portable electronic device may be shortened using the control message. It may be possible, for example, to increase transmission power of the portable electronic device 106 using the control message.

According to yet another embodiment, the apparatus carrying out the embodiments comprises a circuitry including at least one processor and at least one memory including computer program code. When activated, the circuitry causes the apparatus to perform at least some of the functionalities according to any one of the embodiments, or operations thereof.

As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware. The term 'circuitry' would also cover, for example and if applicable to the particular element, a baseband integrated circuit or applications processor integrated circuit for a mobile phone or a similar integrated circuit in a server, a cellular network device, or another network device.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chip set (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, described with regard thereto, and they are not limited to the precise configurations set forth in the given figures, as will be appreciated by one skilled in the art.

Embodiments as described may also be carried out in the form of a computer process defined by a computer program. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The distribution medium may be non-transitory, for example. The computer program medium may be, for example but not limited to, a record medium, computer memory, read-only memory, electrical carrier signal, telecommunications signal, and software distribution package, for example. Coding of software for carrying out the embodiments as shown and described is well within the scope of a person of ordinary skill in the art.

Even though the invention has been described above with reference to an example according to the accompanying drawings, it is clear that the invention is not restricted thereto but can be modified in several ways within the scope of the appended claims. Therefore, all words and expressions should be interpreted broadly and they are intended to illustrate, not to restrict, the embodiment. It will be obvious to a person skilled in the art that, as technology advances, the inventive concept can be implemented in various ways. Further, it is clear to a person skilled in the art that the described embodiments may, but are not required to, be combined with other embodiments in various ways.

What is claimed is:

1. A wrist device comprising:
   a heart activity circuitry;
   at least one processor; and
   at least one non-transitory memory including a computer program code, wherein the at least one non-transitory memory and the computer program code are configured, with the at least one processor, to cause the wrist device to perform operations comprising:
   measuring, using the heart activity circuitry, heart activity of a user of the wrist device, the wrist device being in a physical exercise mode during the measuring;
   receiving a notification of an event, wherein the notification is indicated to the user;
   in response to receiving the notification, initiating at least one further measurement, if the wrist device is in the physical exercise mode measuring the heart activity of the user;
   determining, based on the at least one further measurement, that a predetermined condition is met; and
   in response to the determining that the predetermined condition is met, performing an action having an effect on the indication of the notification.

2. The wrist device of claim 1, wherein the at least one further measurement is performed by at least one sensor, wherein the at least one sensor has a sampling rate, and wherein the operations further comprise: in response to receiving the notification, changing configuration of the at least one sensor performing the at least one measurement.

3. The wrist device of claim 2, wherein changing the configuration of the at least one sensor comprises shortening the sampling rate of the at least one sensor.

4. The wrist device of claim 1, wherein the operations further comprise:
   prior to receiving the notification of the event, determining a type of the physical activity; and
   changing the configuration of the at least one sensor based at least partly on the type of the physical activity when the notification is received.

5. The wrist device of claim 2, wherein the at least one sensor comprises at least one motion sensor configured to measure motion of the user, wherein the at least one measurement comprises a measurement performed by the at least one motion sensor.

6. The wrist device of claim 2, wherein the at least one sensor comprises an image sensor unit, wherein the at least one measurement comprises a measurement performed by the image sensor unit.

7. The wrist device of claim 1, wherein the determining that the predetermined condition is met comprises detecting a gesture performed by the user of the wrist device.

8. The wrist device of claim 7, wherein the gesture detection comprises detecting a face of the user, and wherein the face detection is enabled by the image sensor unit.

9. The wrist device of claim 8, wherein the image sensor unit comprises an image sensor, and wherein the face detection comprises detecting at least one facial feature of the user.

10. The wrist device of claim 1, further comprising: a communication circuitry configured to enable communication with a portable electronic device, wherein the at least one measurement comprises a measurement based on information obtained from the communication circuitry.

11. The wrist device of claim 10, wherein determining that the predetermined condition is met comprises:
   determining that a detected signal strength, by the wrist device, of a transmission, by the portable electronic device, is under a threshold; and
   determining that the detected signal strength of the transmission increases over the threshold.

12. The wrist device of claim 10, wherein the determining that the predetermined condition is met comprises:
   determining that the detected signal strength, by the wrist device, of the transmission, by the portable electronic device, is over the threshold.

13. The wrist device of claim 12, wherein the determining that the predetermined condition is met further comprises:
   in response to the determining that the detected signal strength of the transmission is over the threshold, initiating the gesture detection, wherein the gesture detection comprises detecting that the user reaches for the portable electronic device, and wherein the detection of the reaching is based on the measurement by the at least one motion sensor.

14. The wrist device of claim 10, wherein the communication circuitry comprises at least one of a Bluetooth circuitry, a proximity detection circuitry.

15. The wrist device of claim 1, further comprising:
   in response to receiving the notification, shortening interval between measurement points of the at least one measurement.

16. The wrist device of claim 1, wherein the notification is received from a portable electronic device.

17. The wrist device of claim 1, further comprising:
   a notification indication unit configured to indicate the notification to the user of the wrist device by using at least one of a haptic indication, a sound indication, a visual indication.

18. The wrist device of claim 17, wherein the performing the action having the effect on the indication of the notification comprises terminating at least one of the haptic indication, the sound indication, the visual indication of the notification.

19. The wrist device of claim 1, wherein the performing the action having the effect on the indication of the notification comprises transmitting a control message to a portable electronic device, wherein the control message causes the portable electronic device to terminate at least one of a haptic indication, a sound indication, a visual indication of the notification on the portable electronic device.

20. A method comprising:
   measuring, by a wrist device using a heart activity circuitry, heart activity of a user, the wrist device being in a physical exercise mode during the measuring;
   receiving, by the wrist device, a notification of an event, wherein the notification is indicated to a user of the wrist device;
   in response to receiving the notification, initiating at least one further measurement, if the wrist device is in the physical exercise mode measuring the heart activity of the user;
   determining, based on the at least one measurement, that a predetermined condition is met; and
   in response to the determining that the predetermined condition is met, performing an action having an effect on the indication of the notification.

21. The wrist device of claim 1, wherein the at least one measurement is performed by at least one sensor, and wherein the operations further comprise:
   in response to receiving the notification, changing configuration of the at least one sensor performing the at least one measurement;
   determining whether the user of the wrist device is performing a physical activity; and
   if the user is performing the physical activity, initiating the at least one measurement in response to receiving the notification.

22. The wrist device of claim 1, wherein the at least one measurement is performed by at least one sensor, and wherein the operations further comprise:
   in response to receiving the notification, changing configuration of the at least one sensor performing the at least one measurement;
   determining whether the user of the wrist device is performing a physical activity;
   if the user is performing the physical activity, initiating the at least one measurement in response to receiving the notification;
   determining a type of the physical activity; and
   changing the configuration of the at least one sensor based at least partly on the type of the physical activity when the notification is received.

23. The wrist device of claim 1, wherein the at least one measurement is performed by at least one sensor, and wherein the operations further comprise:
   in response to receiving the notification, changing configuration of the at least one sensor performing the at least one measurement, wherein the at least one sensor comprises at least one motion sensor configured to measure motion of the user, wherein the at least one measurement comprises a measurement performed by the at least one motion sensor.

24. The wrist device of claim 1, wherein the at least one measurement is performed by at least one sensor, and wherein the operations further comprise:

in response to receiving the notification, changing configuration of the at least one sensor performing the at least one measurement;

determining whether the user of the wrist device is performing a physical activity;

if the user is performing the physical activity, initiating the at least one measurement in response to receiving the notification;

determining a type of the physical activity;

changing the configuration of the at least one sensor based at least partly on the type of the physical activity when the notification is received; and in response to receiving the notification, changing configuration of the at least one sensor performing the at least one measurement, wherein the at least one sensor comprises at least one motion sensor configured to measure motion of the user, wherein the at least one measurement comprises a measurement performed by the at least one motion sensor.

25. A wrist device comprising:
a heart activity circuitry configured to perform at least one measurement;
at least one processor; and
at least one non-transitory memory including a computer program code, wherein the at least one non-transitory memory and the computer program code are configured, with the at least one processor, to cause the wrist device to perform operations comprising:
receiving a notification of an event;
in response to receiving the notification, determining, based on the at least one measurement by the heart activity circuitry, a heart rate variation of a user of the wrist device;
determining, based on the measured heart rate variation of the user, that a predetermined condition is met; and
in response to the determining that the predetermined condition regarding the heart rate variation is met, indicating the notification to the user, otherwise not indicating the notification to the user.

* * * * *